(12) United States Patent
Erramilli et al.

(10) Patent No.: US 10,653,457 B2
(45) Date of Patent: May 19, 2020

(54) MULTI-FUNCTION DRIVER INSTRUMENTS AND RELATED METHODS

(71) Applicant: Medos International Sarl, Le Locle (CH)

(72) Inventors: Seetal Erramilli, Mulgrave (AU); Frank Spratt, Middleboro, MA (US); Grant Mellor, Eltham (AU); Areeb Hassan, Narre Warren East (AU); Joanna Talis, Lane Cove (AU); Peter McMahon, Mulgrave (AU)

(73) Assignee: Medos International Sarl, Le Locle (CH)

( * ) Notice: Subject to any disclaimer, the term of this patent is extended or adjusted under 35 U.S.C. 154(b) by 392 days.

(21) Appl. No.: 15/421,490

(22) Filed: Feb. 1, 2017

(65) Prior Publication Data
US 2018/0214190 A1    Aug. 2, 2018

(51) Int. Cl.
*A61B 17/70* (2006.01)
*A61B 17/88* (2006.01)

(52) U.S. Cl.
CPC ...... *A61B 17/7082* (2013.01); *A61B 17/7091* (2013.01); *A61B 17/8875* (2013.01); *A61B 17/8877* (2013.01); *A61B 17/8888* (2013.01); *A61B 17/8894* (2013.01)

(58) Field of Classification Search
CPC ............ A61B 17/7082; A61B 17/7091; A61B 17/8894
See application file for complete search history.

(56) References Cited

U.S. PATENT DOCUMENTS

| 6,736,820 | B2 | 5/2004 | Biedermann et al. | |
| 6,974,460 | B2 | 12/2005 | Carbone et al. | |
| 7,179,261 | B2 | 2/2007 | Sicvol et al. | |
| 7,972,364 | B2* | 7/2011 | Biedermann | A61B 17/7032 606/267 |
| 8,845,649 | B2* | 9/2014 | Jackson | A61B 17/7086 606/99 |
| 2006/0089651 | A1* | 4/2006 | Trudeau | A61B 17/7086 606/86 R |
| 2015/0374418 | A1* | 12/2015 | Martin | A61B 17/1671 606/291 |
| 2017/0181776 | A1* | 6/2017 | Beretta | A61B 17/7032 |

OTHER PUBLICATIONS

[NoAuthorListed] Expedium Verse® Spinal System, System Guide, 2015, 52 pages.

* cited by examiner

*Primary Examiner* — Nicholas W Woodall
(74) *Attorney, Agent, or Firm* — Nutter McClennen & Fish LLP

(57) ABSTRACT

Multi-function driver instruments and related methods are disclosed herein, e.g., for applying a fastener to a bone anchor. In some embodiments, a single instrument can include features for driving multiple different types of fasteners, independently driving multiple different components of a single fastener assembly, and so forth, with the instrument being switchable between multiple operating modes to select the feature needed for a particular function. The instrument can include features for retaining a fastener to the instrument, e.g., during initial insertion of the fastener.

17 Claims, 11 Drawing Sheets

MULTI-FUNCTION DRIVER INSTRUMENTS AND RELATED METHODS

FIELD

Multi-function driver instruments and related methods are disclosed herein, e.g., for applying a fastener to a bone anchor.

BACKGROUND

Bone anchors can be used in orthopedic surgery to fix bone during healing, fusion, or other processes. In spinal surgery, for example, bone anchors can be used to secure a rod or other spinal fixation element to one or more vertebrae to rigidly or dynamically stabilize the spine.

A fastener is typically applied to the bone anchor to reduce the rod into a rod seat of the bone anchor, to secure the rod to the bone anchor, or to lock one or more degrees of freedom of the bone anchor. Exemplary fasteners include set screws that are threaded into a proximal end of the bone anchor and closure caps that are secured to the bone anchor by quarter-turn rotation. A driver instrument is generally used to apply the fastener by applying a rotation force to the fastener.

It is not uncommon for multiple fasteners of different types to be used in the same procedure. Accordingly, it is typically necessary for multiple different types of driver instruments to be available to the surgeon. Multi-component fasteners may also be used, in which case a different driver instrument is typically needed for each component of the fastener. For example, a bone anchor can include a dual set screw in which an outer set screw is used to lock polyaxial movement of the bone anchor and an inner set screw is used to lock a rod to the bone anchor. When such fasteners are used, separate driver instruments for the inner and outer set screws are typically needed.

Also, when installing the fastener, the surgeon must be careful not to drop the fastener into the surgical site, particularly in the case of minimally-invasive procedures where it can be difficult to retrieve a dropped fastener. To reduce this risk, inserter instruments configured to positively retain the fastener during initial insertion are often used.

It can be cumbersome and time-consuming for the surgeon to continually switch between multiple separate driver instruments and/or inserter instruments, potentially leading to surgeon fatigue, poor ergonomics, and lengthened surgical times.

SUMMARY

Multi-function driver instruments and related methods are disclosed herein, e.g., for applying a fastener to a bone anchor. In some embodiments, a single instrument can include features for driving multiple different types of fasteners, independently driving multiple different components of a single fastener assembly, and so forth, with the instrument being switchable between multiple operating modes to select the feature needed for a particular function. The instrument can include features for retaining a fastener to the instrument, e.g., during initial insertion of the fastener.

In some embodiments, a driver instrument can include an inner driver shaft having an inner drive tip; and an outer driver shaft in which the inner driver shaft is at least partially disposed, the outer driver shaft having an outer drive tip. The instrument can have a first configuration in which the inner drive tip is retracted proximally from the outer drive tip and an input torque applied to the inner driver shaft is transferred to the outer driver shaft and the outer drive tip. The instrument can have a second configuration in which the inner drive tip is advanced distally from the outer drive tip and an input torque applied to the inner driver shaft is not transferred to the outer driver shaft or the outer drive tip.

The instrument, in the first configuration, can be configured to apply torque to an outer set screw of a fastener independently from an inner set screw of the fastener and, in the second configuration, can be configured to apply torque to the inner set screw of the fastener independently from the outer set screw. The instrument can be movable between the first and second configurations by translating the inner driver shaft longitudinally relative to the outer driver shaft. The inner driver shaft can include an anti-rotation feature configured to selectively engage a corresponding anti-rotation feature of the outer driver shaft to lock relative rotation between the inner and outer driver shafts and transfer torque between the inner and outer driver shafts. The anti-rotation feature of the inner driver shaft can include an external spline. The anti-rotation feature of the outer driver shaft can include an internal spline.

The outer driver shaft can be configured to retain a fastener to the instrument. The outer driver shaft can include a plurality of resilient fingers extending distally therefrom, at least one of the fingers being configured to clamp onto a fastener received within a distal aperture of the outer driver shaft. At least one of the fingers can include a projection extending radially-inward therefrom and configured to be received within a corresponding recess of a fastener. Each finger can interlock with an adjacent finger at multiple points along its length. The outer driver shaft can have a cut-out formed therein, the cut-out being shaped such that a first finger on one side of the cut-out has an edge that defines one or more recesses, and a second finger on the opposite side of the cut-out has an edge that defines one or more projections, each of the projections being disposed within a corresponding one of the recesses, the edges being defined by the same cut-out. Each projection can include a head portion that is enlarged as compared to a neck portion of the recess in which the projection is disposed, such that the head portion cannot pass through the neck portion.

The instrument can include a locking mechanism configured to selectively lock the instrument in the first configuration or the second configuration. The locking mechanism can include a button movably coupled to the outer driver shaft, the button having an engaged position in which the button interferes with relative longitudinal translation between the inner and outer driver shafts and a disengaged position in which the button does not interfere with relative longitudinal translation between the inner and outer driver shafts. The button can define an opening through which the inner driver shaft extends. A central longitudinal axis of the opening can be collinear with a central longitudinal axis of the inner driver shaft when the button is in the disengaged position. The central longitudinal axis of the opening can be offset from the central longitudinal axis of the inner driver shaft when the button is in the engaged position.

The instrument can be included in a system that includes a fastener having an outer set screw with a first drive feature and an inner set screw threadably mounted in the outer set screw and having a second drive feature. The outer drive tip of the instrument can be configured to apply torque to the outer set screw via the first drive feature and the inner drive tip of the instrument can be configured to apply torque to the inner set screw via the second drive feature.

In some embodiments, a method of applying a fastener to an anchor using a driver instrument having an inner driver shaft with an inner drive tip and an outer driver shaft with an outer drive tip can include positioning the instrument in a first configuration in which the outer drive tip is engaged with a drive feature of an outer component of the fastener and the inner drive tip is not engaged with the fastener; positioning the fastener at least partially within the anchor; rotating the inner driver shaft to transfer torque to the outer drive tip and rotate the outer component of the fastener relative to the anchor; positioning the instrument in a second configuration in which the outer drive tip is engaged with the drive feature of the outer component of the fastener and the inner drive tip is engaged with a drive feature of an inner component of the fastener; and rotating the inner driver shaft to rotate the inner component of the fastener relative to the outer component of the fastener and relative to the anchor.

Rotating the outer component of the fastener relative to the anchor can lock a degree of freedom of the anchor. Rotating the inner component of the fastener relative to the outer component of the fastener can lock a rod to the anchor. The method can include applying a countertorque force to the outer driver shaft while rotating the inner driver shaft to rotate the inner component of the fastener. The method can include retaining the fastener to the instrument. Retaining the fastener can include inserting a portion of the fastener into an aperture defined by a plurality of fingers of the instrument, thereby moving the fingers radially-outward and causing the fingers to clamp radially-inward onto the fastener. Each finger can include a projection received within a recess of an adjacent finger, the projection and the recess interlocking to limit relative movement of the fingers. Positioning the instrument in the second configuration can include adjusting a relative longitudinal position of the inner and outer driver shafts. The method can include positioning the instrument in a third configuration in which the inner drive tip is engaged with a drive feature of a second fastener and the outer drive tip is not engaged with the second fastener; and rotating the inner driver shaft to rotate the second fastener relative to a second anchor and thereby tighten the second fastener to the second anchor.

DETAILED DESCRIPTION

Multi-function driver instruments and related methods are disclosed herein, e.g., for applying a fastener to a bone anchor. In some embodiments, a single instrument can include features for driving multiple different types of fasteners, independently driving multiple different components of a single fastener assembly, and so forth, with the instrument being switchable between multiple operating modes to select the feature needed for a particular function. The instrument can include features for retaining a fastener to the instrument, e.g., during initial insertion of the fastener.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Prior Art Bone Anchor

Figure 1A:
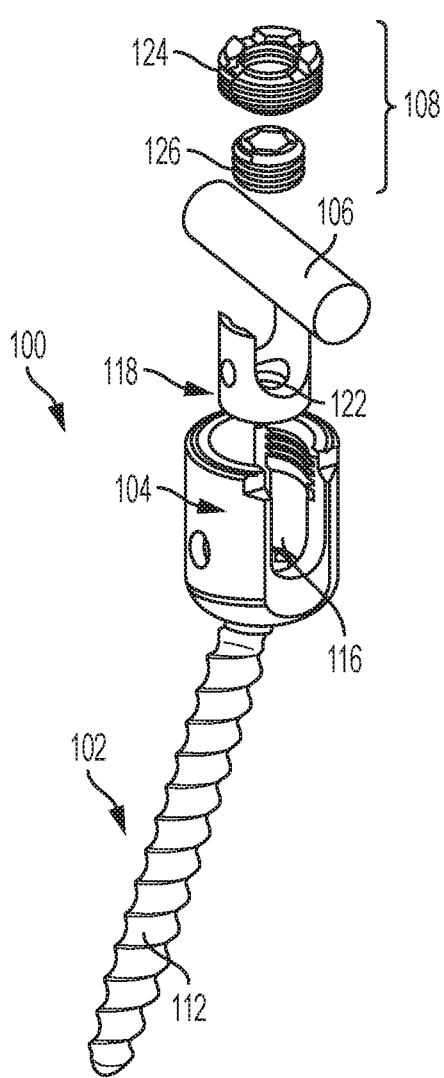
FIG. 1A is an exploded perspective view of a prior art bone anchor.
Figure 1B:
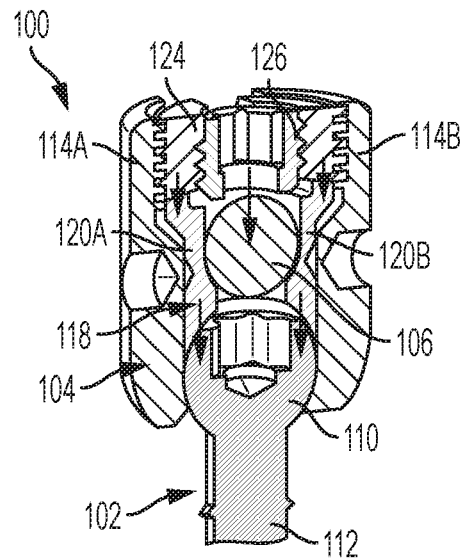
FIG. 1B is a sectional perspective view of the bone anchor of FIG. 1A.
Figure 1C:
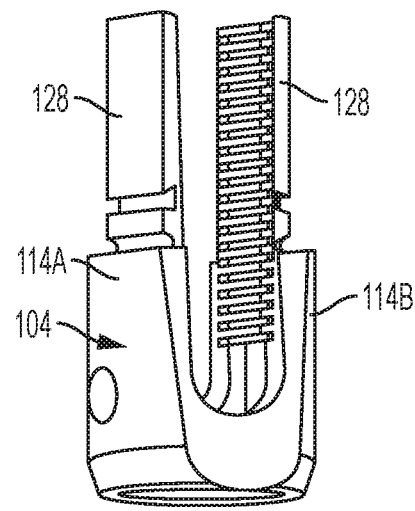
FIG. 1C is a perspective view of a receiver member of the bone anchor of FIG. 1A, shown with reduction tabs.
Figure 2A:
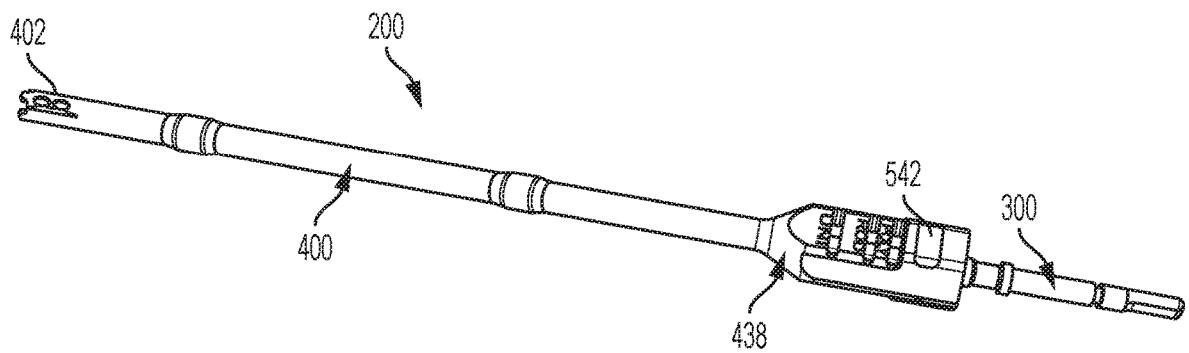
FIG. 2A is a perspective view of a driver instrument.
Figure 2B:
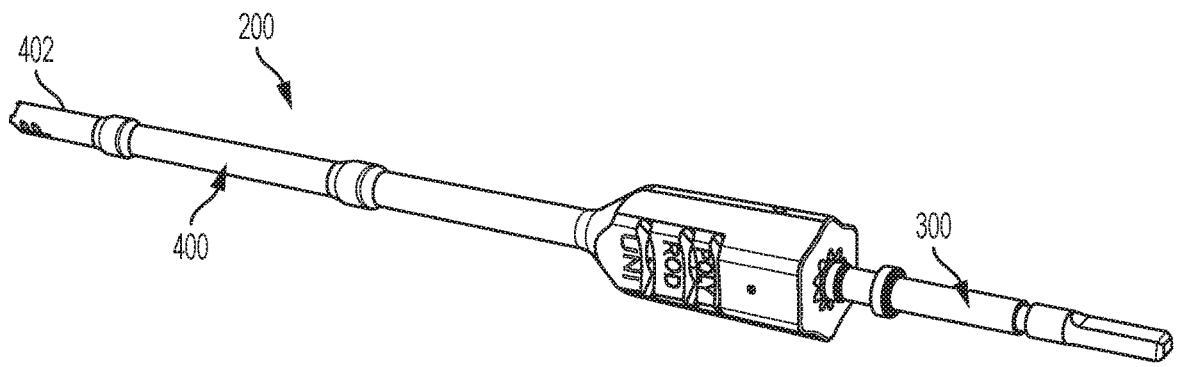
FIG. 2B is another perspective view of the instrument of FIG. 2A.
Figure 2C:
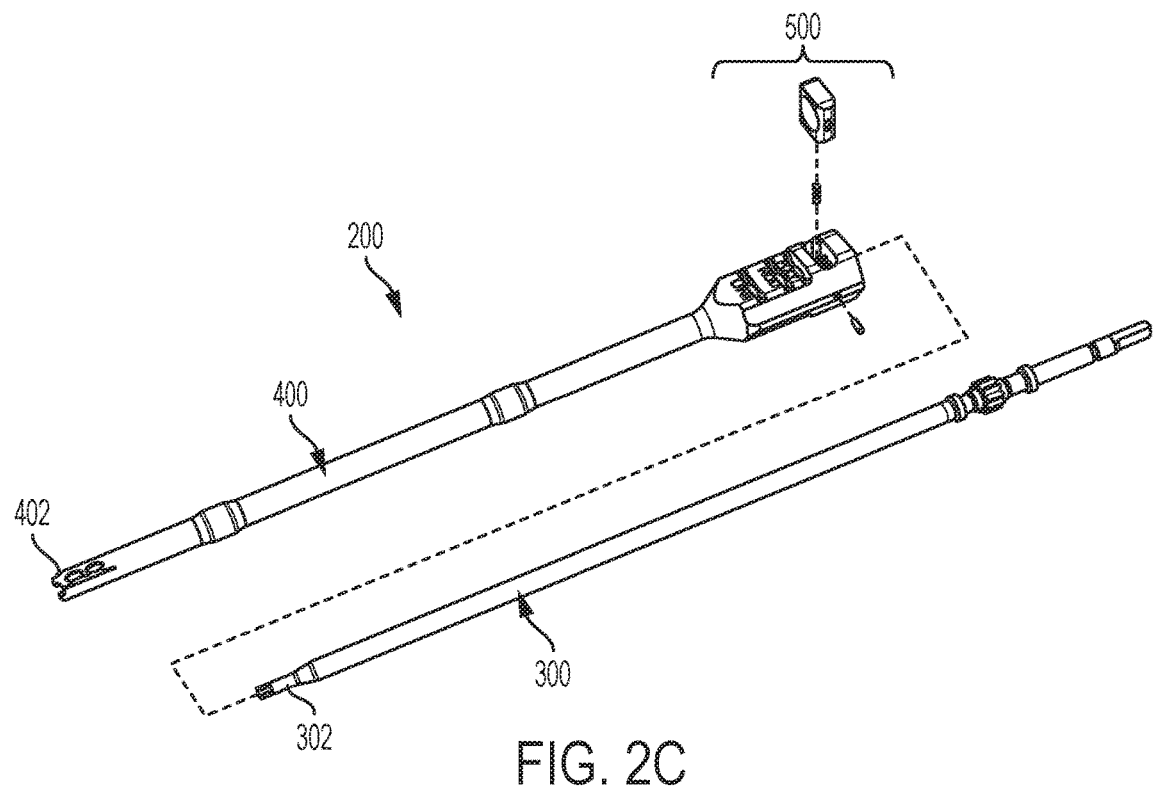
FIG. 2C is an exploded perspective view of the instrument of FIG. 2A.
Figures 2D, 2E, 2F, 2G:
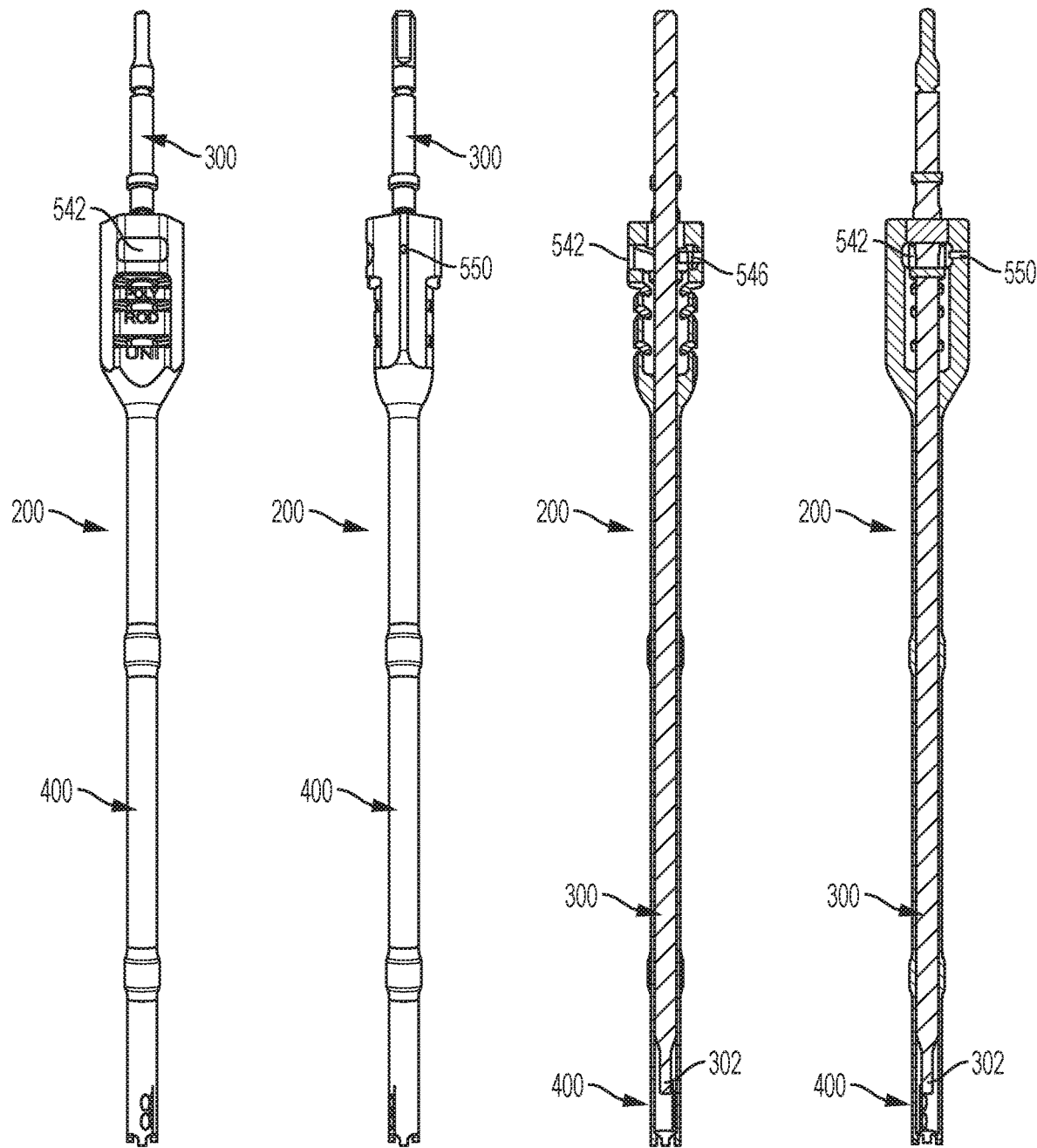
FIG. 2D is a top view of the instrument of FIG. 2A.
FIG. 2E is a side view of the instrument of FIG. 2A.
FIG. 2F is a sectional side view of the instrument of FIG. 2A.
FIG. 2G is a sectional top view of the instrument of FIG. 2A.

FIGS. 1A-1C illustrate a prior art bone anchor 100 with which one or more of the instruments described herein can be used. It will be appreciated that the illustrated bone anchor 100 is exemplary and that the instruments described below can be used with any of a variety of bone anchors.

The illustrated bone anchor 100 includes an anchor portion or shank 102, a head or receiver member 104 for receiving a spinal fixation element, such as a spinal rod 106, to be coupled to the shank 102, and a fastener or closure mechanism 108 to capture a spinal fixation element within the receiver member and fix the spinal fixation element with respect to the receiver member. The shank 102 includes a proximal head 110 and a distal shaft 112 configured to engage bone. The receiver member 104 has a proximal end having a pair of spaced apart arms 114A, 114B defining a recess or channel 116 therebetween and a distal end having a distal end surface defining an opening through which at least a portion of the shank 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the shank 102 is generally in the shape of a truncated sphere having a planar proximal surface and an approximately spherically-shaped distal surface. The illustrated bone anchor 100 is a polyaxial bone screw designed for posterior implantation in the pedicle or lateral mass of a vertebra. The proximal head 110 of the shank 102 engages the distal end of the receiver member 104 in a ball and socket like arrangement in which the proximal head and the distal shaft 112 can pivot relative to the receiver member. The distal surface of the proximal head 110 of the shank 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the shank 102 can be configured to engage bone and, in the illustrated embodiment, includes an external bone engaging thread. The distal shaft 112 can also include other structures for engaging bone, including a hook. The distal shaft 112 of the shank 102 can be cannulated, having a central passage or cannula extending the length of the shank to facilitate delivery of the shank over a guidewire in, for example, minimally-invasive procedures. Other components of the bone anchor 100, including, for example, the closure mechanism 108, the receiver member 104, and the compression member or cap 118 (discussed below) can be cannulated or otherwise have an opening to permit delivery over a guidewire.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the shank 102 extends. For example, the distal shaft 112 of the shank 102 can extend through the opening.

The shank 102 can be selectively fixed relative to the receiver member 104. Prior to fixation, the shank 102 is movable relative to the receiver member 104 within a cone of angulation generally defined by the geometry of the distal end of the receiver member and the proximal head 110 of the shank 102. The bone anchor 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor 100 can be a conventional (non-biased) polyaxial screw in which the shank 102 pivots in the same amount in every direction.

The spinal fixation element, e.g., the spinal rod 106, can either directly contact the proximal head 110 of the shank 102 or can contact an intermediate element, e.g., a compression member 118. The compression member 118 can be positioned within the receiver member 104 and interposed between the spinal rod 106 and the proximal head 110 of the shank 102 to compress the distal outer surface of the proximal head into direct, fixed engagement with the distal inner surface of the receiver member 104. The compression member 118 can include a pair of spaced apart arms 120A and 120B defining a U-shaped seat 122 for receiving the spinal rod 106 and a distal surface for engaging the proximal head 110 of the shank 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the shank 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the compression member 118 and an inner set screw 126 operable to act on the rod 106. Various other closure mechanisms 108 can be used instead or in addition, such as a nut that extends around an outer circumference of the receiver member 104, a cap or fastener that slides onto the receiver member from the side, or a cap or fastener that locks to the receiver member by quarter-turn rotation. The receiver member 104 can include, can be formed integrally with, or can be coupled to one or more extension tabs 128 (shown in FIG. 1C) that extend proximally from the receiver member 104 to functionally extend the length of the arms 114A, 114B. The extension tabs 128 can facilitate installation and assembly of a fixation or stabilization construct and can be removed prior to completing a surgical procedure.

The bone anchor 100 can be used with a spinal fixation element such as rigid spinal rod 106. Alternatively, the spinal fixation element can be a dynamic stabilization member that allows controlled mobility between the instrumented vertebrae.

In use, the bone anchor 100 can be assembled such that the distal shaft 112 extends through the opening in the distal end of the receiver member 104 and the proximal head 110 of the shank 102 is received in the distal end of the receiver member 104. A driver instrument can be fitted with the shank 102 to drive the shank into bone. The compression member 118 can be positioned within the receiver member 104 such that the arms 120A, 120B of the compression member are aligned with the arms 114A, 114B of the receiver member 104 and the lower surface of the compression member 118 is in contact with the proximal head 110 of the shank 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the compression member 118 onto the proximal head 110 of the shank 102, thereby locking the angular position of the shank 102 relative to the receiver member 104. A torsional force can be applied to the inner set screw 126 to force the spinal rod 106 into engagement with the compression member 118 and thereby fix the spinal rod 106 relative to the receiver member 104. In arrangements with a single set screw, a torsional force can be applied to the set screw both to lock the angular position of the shank 102 relative to the receiver member 104 and to fix the spinal rod 106 relative to the receiver member 104.

The driver instruments disclosed herein can be configured to operate in conjunction with bone anchors of the type described above or various other types known in the art. Exemplary bone anchors with which the driver instruments disclosed herein can be used include monoaxial screws, polyaxial screws, uniplanar screws, and favored-angle screws.

Multi-Function Driver Instruments and Related Methods

Figure 4A:
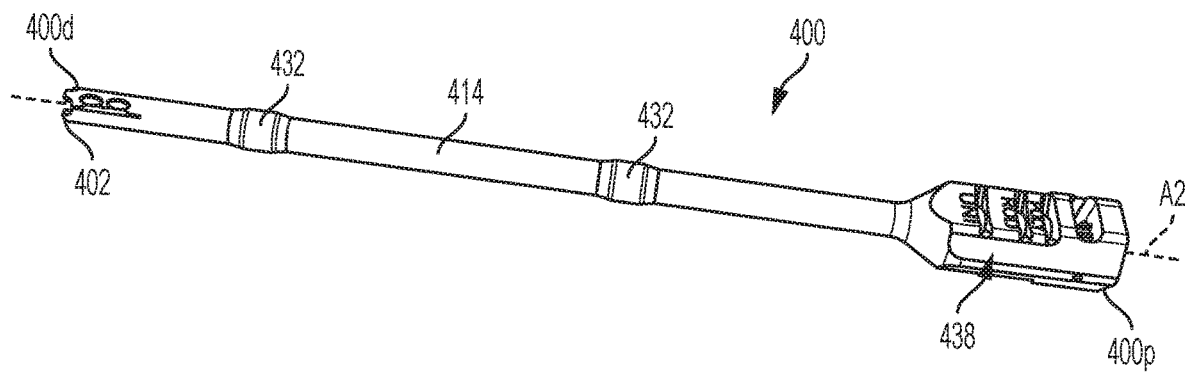
FIG. 4A is a perspective view of an outer driver shaft of the instrument of FIG. 2A.
Figure 4B:
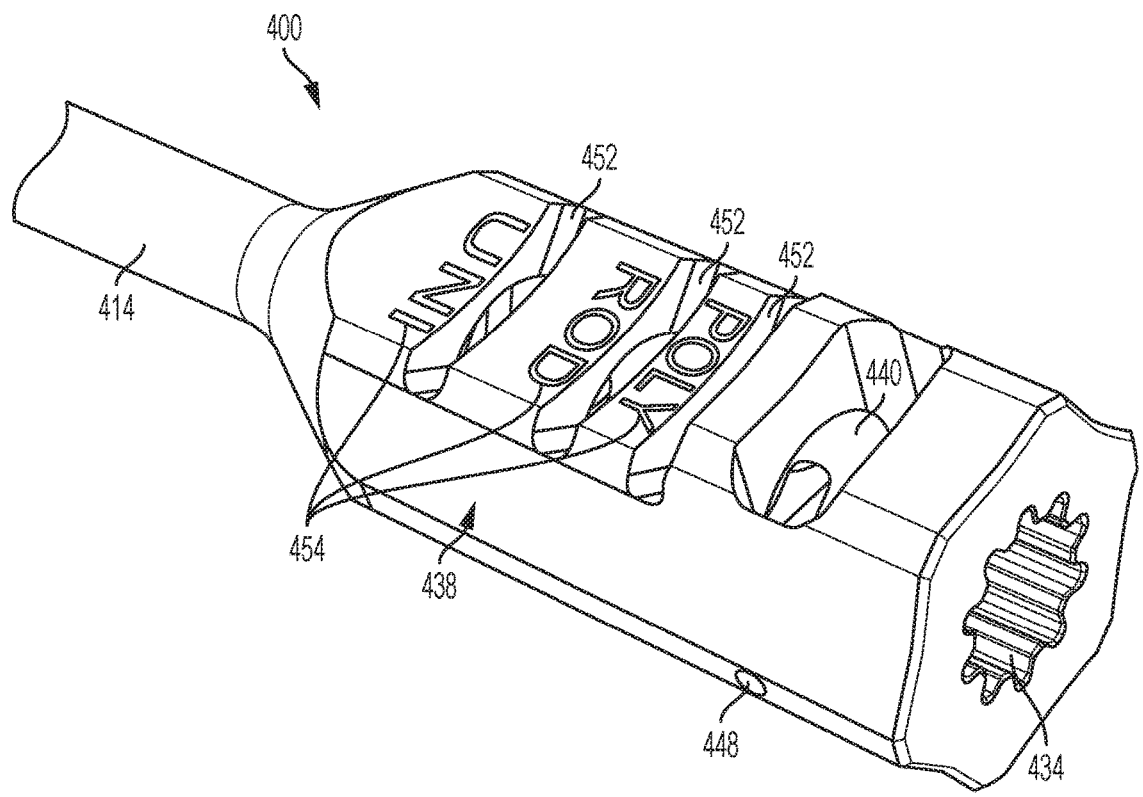
FIG. 4B is a perspective view of the proximal end of the outer driver shaft of FIG. 4A.
Figure 4C:
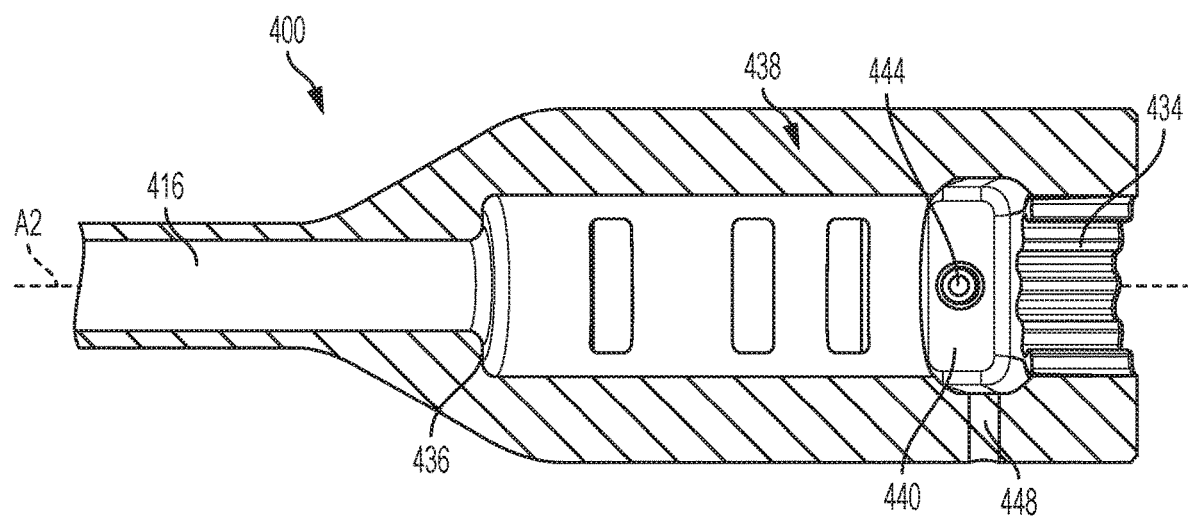
FIG. 4C is a sectional top view of the proximal end of the outer driver shaft of FIG. 4A.
Figure 4D:
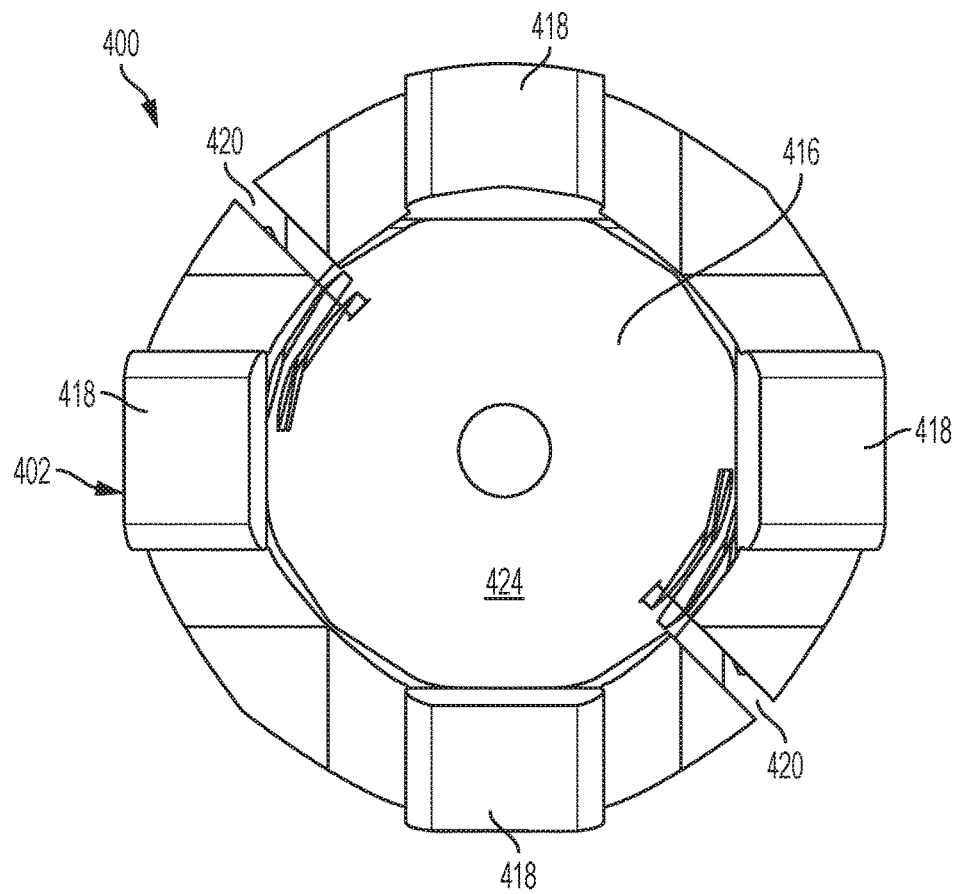
FIG. 4D is an end view of the outer driver shaft of FIG. 4A.
Figure 4E:
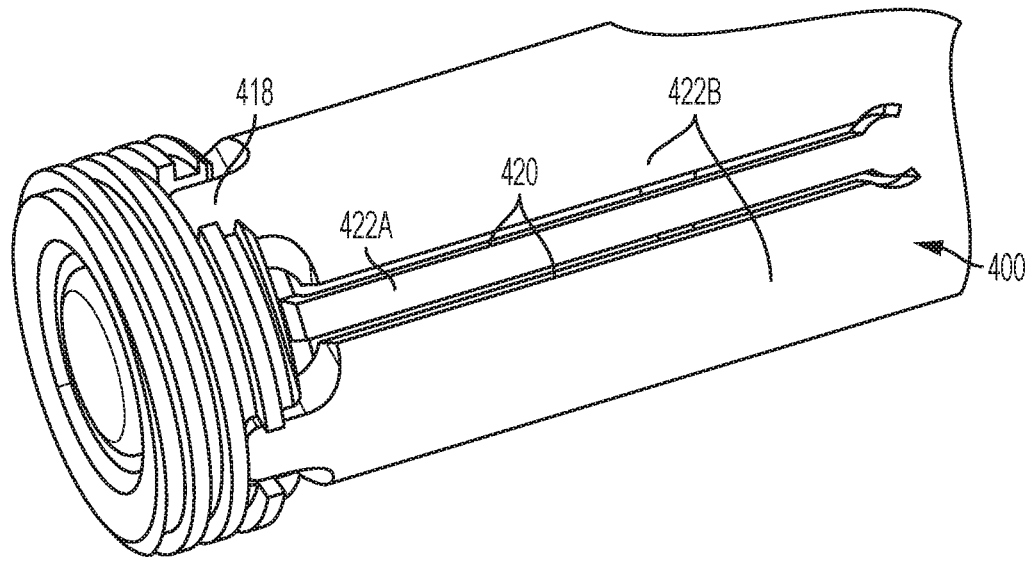
FIG. 4E is a perspective view of the distal end of the outer driver shaft of the instrument of FIG. 2A, shown with a first retention feature and a fastener.
Figure 4F:
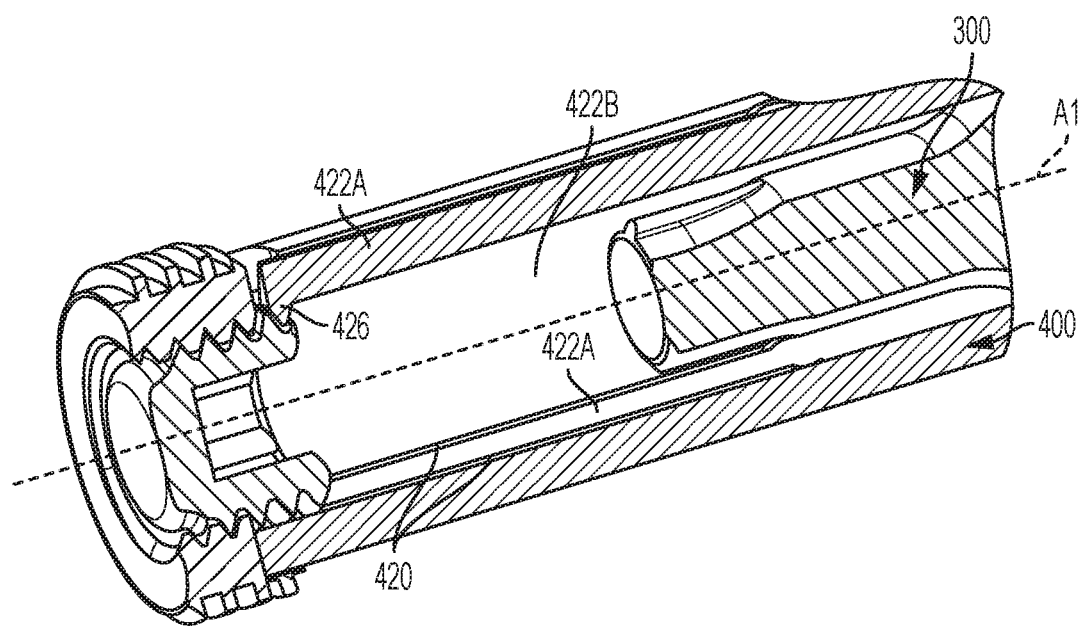
FIG. 4F is a sectional perspective view of the retention feature and fastener of FIG. 4E.
Figure 4G:
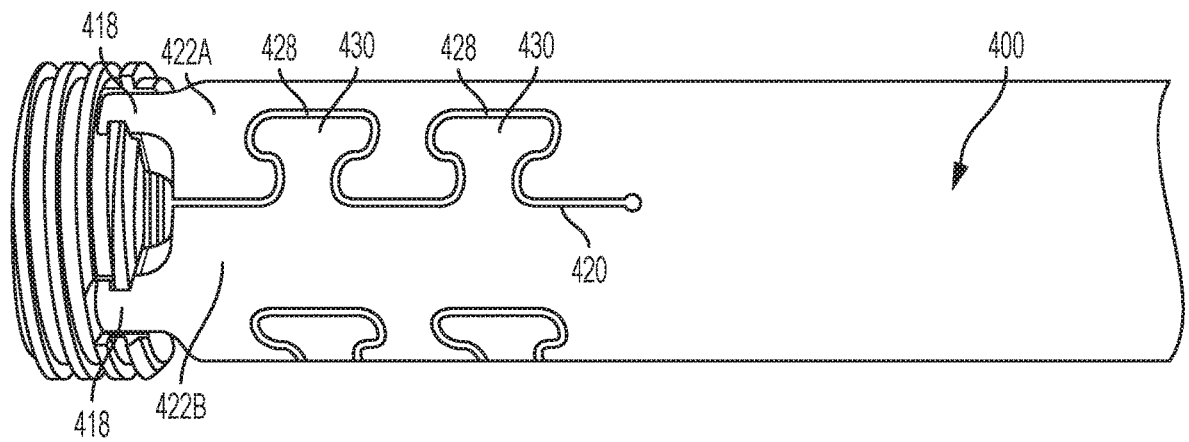
FIG. 4G is a perspective view of the distal end of the outer driver shaft of the instrument of FIG. 2A, shown with a second retention feature and a fastener.

FIGS. 2A-2G illustrate an exemplary embodiment of a driver instrument 200 that can be used, for example, to apply a fastener to a bone anchor. As shown, the instrument 200 can include an inner driver shaft 300 and an outer driver shaft 400. An inner drive tip 302 can be formed at the distal end of the inner driver shaft 300. An outer drive tip 402 can be formed at the distal end of the outer driver shaft 400. Either or both of the inner and outer drive tips 302, 402 can be configured to facilitate retention of a fastener to the instrument 200. The instrument 200 can include a locking mechanism 500 configured to selectively lock the inner driver shaft 300 in one of a plurality of longitudinal positions relative to the outer driver shaft 400, thereby selecting an operating mode of the instrument 200. For example, the instrument 200 can be configured such that only the outer drive tip 402 engages a fastener (e.g., as shown in FIG. 7B), such that both the inner and outer drive tips 302, 402 engage a fastener (e.g., as shown in FIG. 7C), or such that only the inner drive tip 302 engages a fastener (e.g., as shown in FIG. 8B). The same instrument 200 can thus be used to independently drive inner and outer components of a multi-component fastener (e.g., a dual set screw of the type shown in FIG. 7A), or to drive a unitary fastener (e.g., a single set screw of the type shown in FIG. 8A). The instrument 200 can include features for retaining a fastener to the instrument, for example as shown in FIGS. 4E-4G.

Figure 3A:
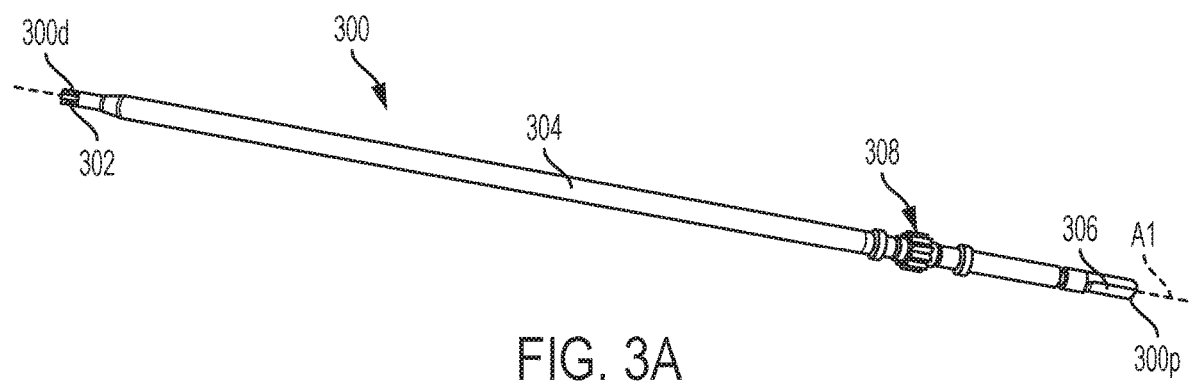
FIG. 3A is a perspective view of an inner driver shaft of the instrument of FIG. 2A.
Figure 3B:
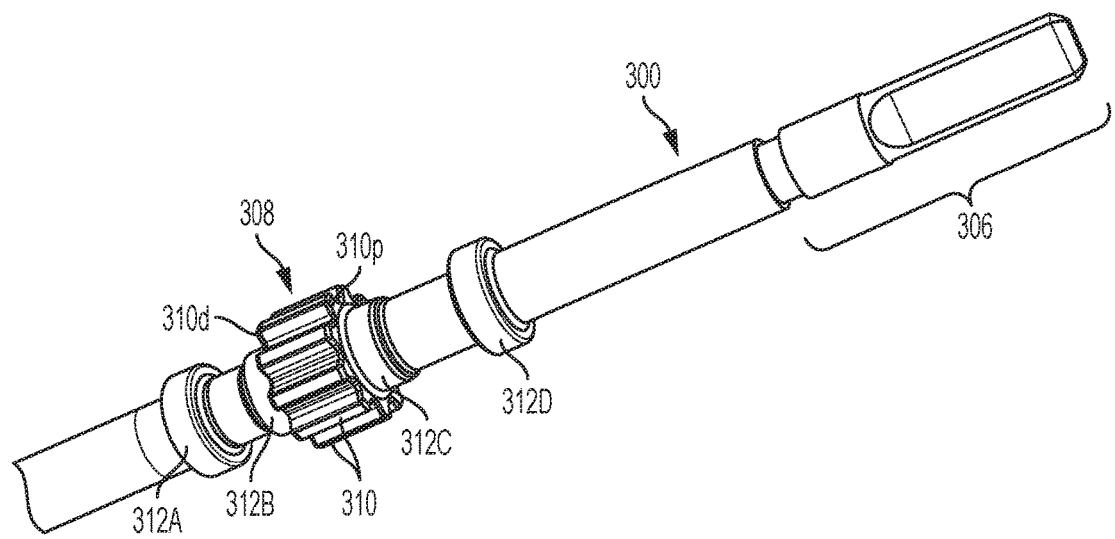
FIG. 3B is a perspective view of the proximal end of the inner driver shaft of FIG. 3A.

The inner driver shaft 300 is shown in greater detail in FIGS. 3A-3B. As shown, the inner driver shaft 300 can include an elongate, generally-cylindrical body 304 having a proximal end 300p and a distal end 300d and extending along a central longitudinal axis A1. The body 304 of the driver shaft 300 can be solid or can be cannulated to allow passage of a guidewire therethrough.

The proximal end 300p of the inner driver shaft 300 can include a modular coupling 306 for selectively attaching the inner driver shaft to a structure or device for applying a rotational force to the inner driver shaft about the longitudinal axis A1. For example, the modular coupling 306 can be configured to attach the inner driver shaft 300 to a handle or knob configured to be grasped by a user, to a powered device such as an electric or pneumatic drill or driver, or to a surgical robot. In other embodiments, the inner driver shaft 300 can include a handle formed integrally therewith. Exemplary handles include pencil-type handles, palm-grip handles, T-handles, and the like.

The distal end 300d of the inner driver shaft 300 can include an inner drive tip 302 for engaging a corresponding drive interface of a fastener and for transferring rotational force applied to the inner driver shaft to the fastener. Exemplary drive tips include Phillips, slotted, hexalobe, Torx®, hexagonal, pentalobe, and the like, of various standard or non-standard sizes. The drive tip 302 can also include a modular connector such that any of a plurality of drive tips having different types or sizes can be selectively coupled to the distal end of the inner driver shaft 300.

The inner driver shaft 300 can include one or more anti-rotation features. The anti-rotation feature can be selectively engaged with a corresponding anti-rotation feature of the outer driver shaft 400 to limit or prevent rotation of the inner driver shaft relative to the outer driver shaft about the axis A1, and to allow torque transfer from the inner driver shaft to the outer driver shaft and vice versa. In the illustrated embodiment, the inner driver shaft 300 includes an anti-rotation feature in the form of an external spline 308. The spline 308 can include a plurality of teeth 310 projecting radially-outward from the inner driver shaft 300. The teeth 310 can be linear and can extend parallel to the axis A1. The teeth 310 can collectively define a proximal abutment surface 310p and a distal abutment surface 310d. The abutment surfaces 310p, 310d can be planar or substantially planar as shown and can extend perpendicular or substantially perpendicular to the axis A1. Proximal and distal ends of the teeth 310 can be ramped, rounded, or otherwise tapered to facilitate insertion of the external spline 308 into an internal spline 434 of the outer driver shaft 400, as described further below. While an external spline 308 is shown, it will be appreciated that any of a variety of anti-rotation features can be used instead or in addition. In some embodiments, the anti-rotation feature can be or can include a non-cylindrical portion of the inner driver shaft 300. In some embodiments, the anti-rotation feature can be or can include a square, rectangular, triangular, or hexagonal portion of the inner driver shaft 300. Use of a spline having a plurality of teeth as shown can advantageously increase the number of rotational positions about the axis A1 at which the anti-rotation feature of the inner driver shaft 300 is aligned for insertion into the anti-rotation feature of the outer driver shaft 400. Use of a spline can also provide increased torsional strength as compared to other anti-rotation features.

The inner driver shaft 300 can include one or more anti-translation features. The anti-translation features can be selectively engaged with corresponding anti-translation features of the outer driver shaft 400 and/or the locking mechanism 500 to limit or prevent longitudinal translation of the inner driver shaft 300 relative to the outer driver shaft along the axis A1. In the illustrated embodiment, the inner driver shaft 300 includes anti-translation features in the form of a plurality of annular projections 312 that extend radially-outward from the inner driver shaft 300. In particular, the illustrated inner driver shaft 300 includes a first projection 312A, a second projection 312B, a third projection 312C, and a fourth projection 312D. The number of projections 312 can vary, for example depending on the number of operating modes of the instrument 200. The projections 312 can each define a proximal abutment surface, a distal abutment surface, or both proximal and distal abutment surfaces. The abutment surfaces of the projections 312 can be planar or substantially planar as shown and can extend perpendicular or substantially perpendicular to the axis A1. While annular projections 312 are shown, it will be appreciated that any of a variety of anti-translation features can be used instead or in addition, such as grooves, recesses, pins, etc. As described further below, the abutment surfaces of the spline teeth 310 and/or the projections 312 can engage corresponding abutment surfaces of the outer driver shaft 400 and/or the locking mechanism 500 to lock the inner driver shaft 300 in a fixed or substantially fixed longitudinal position relative to the outer driver shaft 400.

The inner driver shaft 300 can include external markings (not shown) or mechanical features (e.g., the spline 308) which can be aligned with openings formed in the outer driver shaft 400 to provide a visual indication to the user as to the relative longitudinal positions of the inner and outer driver shafts 300, 400 and thus the current operating mode of the instrument 200. The markings can be stamped, printed, painted, or otherwise formed on or attached or adhered to an exterior surface of the inner driver shaft 300. In some embodiments, the markings can be formed by a section of the inner driver shaft 300 having a different color from the other portions of the inner driver shaft.

The outer driver shaft 400 is shown in greater detail in FIGS. 4A-4G. As shown, the outer driver shaft 400 can include an elongate, generally-cylindrical body 414 having a proximal end 400p and a distal end 400d and extending along a central longitudinal axis A2. The outer driver shaft 400 can define a central passage 416 extending between the proximal and distal ends 400p, 400d. The inner driver shaft 300 can be coaxially received within the central passage 416, such that the central axis A2 of the outer driver shaft 400 is collinear with the central axis A1 of the inner driver shaft 300.

The distal end 400d of the outer driver shaft 400 can include an outer drive tip 402 for engaging a corresponding drive interface of a fastener and for transferring rotational force applied to the outer driver shaft to the fastener. Exemplary drive tips include Phillips, slotted, hexalobe, Torx®, hexagonal, pentalobe, and the like, of various standard or non-standard sizes. The drive tip 402 can also include a modular connector such that any of a plurality of drive tips having different types or sizes can be selectively coupled to the distal end of the outer driver shaft 400. The illustrated drive tip 402 is a castle-type drive feature. As shown, the drive tip 402 can include a plurality of distally-extending teeth 418 spaced about the circumference of a distal-facing end surface of the outer driver shaft 400. While four teeth 418 are shown spaced 90 degrees apart from one another, it will be appreciated that any number of teeth and any relative spacing can be used.

The outer driver shaft 400 can include features for retaining a fastener to the instrument 200. For example, the outer driver shaft 400 can include one or more cut-outs or slits 420 formed therein to define a plurality of distally-extending fingers 422. The outer driver shaft 400 can be formed from a flexible material to allow the fingers 422 to be deformed or deflected radially-inward and/or radially-outward. The material used to form the fingers 422 can also have resilient properties such that, when moved from a resting position, the fingers are biased back towards said resting position. The distal ends of the fingers 422 can define an aperture 424 configured to receive at least a portion of a fastener therein. The aperture 424 can include at least one dimension that is less than a corresponding dimension of the fastener, such that the fingers 422 are moved radially-outward as the fastener is inserted into the aperture. Resilient properties of the fingers 422 can bias the fingers radially-inward to clamp onto the fastener and thereby retain the fastener to the instrument 200. The fingers 422 can include a ledge or projection 426 extending radially-inward therefrom and configured to positively interlock with a recess or groove of the fastener. For example, one or more of the fingers 422 can include an inwardly-projecting tooth 426 configured to fit within an external thread of the fastener to augment retention of the fastener to the instrument 200. A distal-facing surface of the ledge 426 can be curved, ramped, or otherwise tapered to slide over a leading edge of the fastener and encourage deflection of the fingers 422 to allow fastener insertion into the aperture 424. A proximal-facing surface of the ledge 426 can be curved, ramped, or otherwise tapered to slide over a feature of the fastener and encourage deflection of the fingers 422 to allow for release of the fastener from the instrument 200, e.g., when a proximally-directed axial force is applied to the instrument while the fastener is secured to a bone anchor.

The geometry of the cut-outs 420 that define the fingers 422 can vary. In the arrangement shown in FIGS. 4E-4F, the cut-outs 420 are substantially linear and run parallel to the axis A1. The cut-outs 420 can extend all the way to the terminal distal end of the outer driver shaft 400. The cut-outs 420 can flare outward at their proximal ends to provide stress relief for the living hinge defined by the cut-outs. The cut-outs 420 can be spaced about the circumference of the outer driver shaft 400 to define a plurality of relatively narrow fingers 422A and a plurality of relatively thick fingers 422B. The narrower fingers 422A can define ledges 426 configured to sit within an exterior thread of a fastener, e.g., an inner set screw as shown. The ledges 426 can be conical or convex in cross-section. The thicker fingers 422B can include the teeth 418 used for driving the fastener, e.g., an outer set screw of the fastener as shown. Retention of the fastener to the instrument 200 can be achieved by (i) positive interlock between the ledges 426 of the narrower fingers 422A and the threads of the fastener, (ii) friction between the narrower fingers 422A and the inner set screw generated by the resiliency of the narrower fingers, (iii) friction between the thicker fingers 422B and the inner set screw generated by the resiliency of the thicker fingers, or (iv) any combination of the above.

In the arrangement shown in FIG. 4G, the cut-outs 420 curve back on themselves such that the fingers 422 defined by the cut-outs are interlocked by a "puzzle" feature. The cut-outs 420 can extend all the way to the terminal distal end of the outer driver shaft 400. The cut-outs 420 can flare outward at their proximal ends to provide stress relief for the living hinge defined by the cut-outs. The cut-outs 420 can deviate from a straight line between their proximal and distal ends. The cut-outs 420 can include at least first and second linear segments offset from one another about the circumference of the outer driver shaft 400. The first and second linear segments can be connected by an S-shaped segment. The illustrated arrangement includes three first linear segments and two second linear segments, connected by four S-shaped segments, though it will be appreciated that any number of segments can be included.

As shown in FIG. 4G, the cut-outs 420 can be shaped such that a finger 422A on one side of the cut-out has an edge that defines one or more recesses 428, and a finger 422B on the opposite side of the cut-out has an edge that defines one or more projections 430 disposed within a respective one of the recesses 428, the edges being defined by the same cut-out. Each recess 428 can include a reduced neck portion and each projection 430 can include an enlarged head portion. The head portion of the projection 430 can be larger than the neck portion of the recess 428, such that the head portion cannot pass through the neck portion and thus the projection 430 cannot be removed from the recess 428. Accordingly, the fingers 422A, 422B can be positively interlocked with one another such that the degree to which the fingers can be separated is limited. When the fingers 422 are not interlocked, it is possible that high levels of torque applied to the outer driver shaft 400 could cause the fingers to tilt or to splay too far outward, allowing the teeth 418 of the outer drive tip 402 to slip out of engagement with the fastener, which may be undesirable. Interlocking the fingers 422 can resist the tendency for the fingers to tilt or prevent the fingers from splaying too far outward, advantageously allowing the instrument 200 to remain engaged with the fastener even when high levels of torque are applied. This retention geometry can also allow each of the fingers 422 to be made thicker, further strengthening the instrument 200 for torque application. In some embodiments, the fingers 422 are interlocked with one another at multiple points along the length of the fingers.

The cut-outs 420 of FIG. 4G can be spaced about the circumference of the outer driver shaft 400 to define the plurality of fingers 422. The fingers 422 can define ledges configured to sit within an exterior thread of a fastener, e.g., an inner set screw. The ledges can be conical or convex in cross-section. The fingers 422 can include the teeth 418 used for driving the fastener, e.g., an outer set screw of the fastener as shown. Retention of the fastener to the instrument 200 can be achieved by (i) positive interlock between the ledges of the fingers 422 and the threads of the fastener, (ii) friction between the fingers 422 and the inner set screw generated by the resiliency of the fingers, or (iii) any combination of the above.

While resilient material properties are described above for biasing the fingers 422, it will be appreciated that various other bias features can be used instead or in addition, such as leaf springs, coil springs, and the like. While the above-described fingers 422 are formed integrally with the outer driver shaft 400, it will be appreciated that the fingers can alternatively be separate components joined to the outer driver shaft by a hinge or other joint.

When used with a multi-component fastener, the retention features described herein can advantageously double as a fail-safe to ensure that the initial positioning of the fastener components is correct. For example, in the case of a dual set screw as shown, it is typically desired that the inner set screw sit proud of the outer set screw in the proximal direction during initial insertion and tightening of the outer set screw to prevent premature locking of the rod. The retention features of the instrument 200 can be configured to prevent the fastener from being retained to and picked up by the instrument when the fastener is not configured in this manner. For example, if the inner set screw is flush or sub-flush with the proximal surface of the outer set screw, the instrument 200 can be configured such that the retention features cannot engage the fastener to retain the fastener to the instrument. The inability to retain or pick up the fastener using the instrument 200 can alert the user that the fastener is not in an appropriate initial configuration.

Referring again to FIGS. 4A-4D, the outer driver shaft 400 can include one or more protrusions, bulges, or other areas of increased diameter 432. The protrusions 432 can be configured to support the extension tabs of a bone anchor as a fastener is applied to the bone anchor. Such protrusions 432 can help prevent the extension tabs from bending inward towards the outer driver shaft 400 and breaking off or separating from the bone anchor prematurely. Alternatively, or in addition, the protrusions 432 can help align the instrument 200 and a fastener coupled thereto with the bone anchor, for example by centering the instrument between extension tabs of the bone anchor or within a tubular access device leading to the bone anchor.

The outer driver shaft 400 can include one or more anti-rotation features. The anti-rotation feature can be selectively engaged with a corresponding anti-rotation feature of the inner driver shaft 300 to limit or prevent rotation of the inner driver shaft relative to the outer driver shaft 400 about the axis A1, and to allow torque transfer from the inner driver shaft to the outer driver shaft and vice versa. In the illustrated embodiment, the outer driver shaft 400 includes an anti-rotation feature in the form of an internal spline 434. The spline 434 can include a plurality of teeth projecting radially-inward into the central passage 416 of the outer driver shaft 400. The teeth can be linear and can extend parallel to the axis A2. Proximal and distal ends of the teeth can be ramped, rounded, or otherwise tapered to facilitate insertion of the external spline 308 of the inner driver shaft 300 into the internal spline 434 of the outer driver shaft 400, as described further below. While an internal spline 434 is shown, it will be appreciated that any of a variety of anti-rotation features can be used instead or in addition. In some embodiments, the anti-rotation feature can be or can include a non-cylindrical portion of the central passage 416. In some embodiments, the anti-rotation feature can be or can include a square, rectangular, triangular, or hexagonal portion of the central passage 416. Use of a spline 434 having a plurality of teeth as shown can advantageously increase the number of rotational positions about the axis A2 at which the anti-rotation feature of the inner driver shaft 300 is aligned for insertion into the anti-rotation feature of the outer driver shaft 400. The internal spline 434 can be formed in a proximal end wall of the outer driver shaft 400 as shown, or at any other location along the length of the outer driver shaft. Use of a spline can also provide increased torsional strength as compared to other anti-rotation features.

The outer driver shaft 400 can include one or more anti-translation features. The anti-translation features can be selectively engaged with corresponding anti-translation features of the inner driver shaft 300 to limit or prevent longitudinal translation of the inner driver shaft relative to the outer driver shaft along the axis A2. In the illustrated embodiment, the diameter of the central passage 416 decreases along the length of the outer driver shaft 400 to define a shoulder 436. The shoulder 436 can define a proximal abutment surface that serves as an anti-translation feature. The abutment surface can be planar or substantially planar as shown and can extend perpendicular or substantially perpendicular to the axis A2. While a shoulder 436 is shown, it will be appreciated that any of a variety of anti-translation features can be used instead or in addition, such as grooves, recesses, pins, etc. As described further below, the abutment surface of the shoulder 436 can contact a corresponding abutment surface of the inner driver shaft 300 to limit distal translation of the inner driver shaft and help maintain the inner driver shaft 300 in a fixed or substantially fixed longitudinal position relative to the outer driver shaft 400.

The outer driver shaft 400 can include a housing 438 in which the locking mechanism 500 is disposed. The housing 438 can be formed as an enlarged proximal portion of the outer driver shaft 400 as shown. The housing 438 can define a chamber 440 that is open to a sidewall of the housing and that intersects with the central passage 416. The chamber 440 can be sized and shaped to substantially correspond to the size and shape of an actuation button 542 of the locking mechanism 500. The button 542 can be slidably received within the chamber 440 such that the button can move within the chamber towards and away from the central passage 416, e.g., in a direction perpendicular to the axis A2. The floor of the chamber 440 can include a first bore 444 in which at least a portion of a button spring 546 of the locking mechanism 500 can be received. The housing 438 can include an opening 448 formed in a sidewall of the housing that intersects with the chamber 440. The opening 448 can extend perpendicular to the axis A2 as shown. The opening 448 can be configured to receive at least a portion of a retention pin 550 of the locking mechanism 500 therein.

At least a portion of the central passage 416 formed in the housing 438 can have a diameter that is greater than a maximum outer diameter of the anti-rotation feature(s) of the inner driver shaft 300. Accordingly, when the anti-rotation feature(s) of the inner driver shaft 300 are disposed in this portion of the central passage 416, the inner driver shaft 300 can be free to rotate relative to the outer driver shaft 400 about the axis A1.

One or more openings 452 can be formed in the sidewall of the outer driver shaft 400, which can advantageously allow sterilizing solutions, cleaning agents, or other flowable materials to access the interior of the outer driver shaft. The illustrated outer driver shaft 400 includes a plurality of elongate slits 452 that are open to the central passage 416 and spaced along the length of the housing 438. The openings 452 can also allow visualization of the markings of the inner driver shaft 300, depending on the longitudinal position of the inner driver shaft relative to the outer driver shaft 400, thereby indicating to a user the current operating mode of the instrument 200. The outer driver shaft 400 can include external markings 454 associated with each of the openings 452 to indicate the operating mode of the instrument 200 represented by said opening. For example, a "UNI" label adjacent to the distal-most opening 452 can indicate to the user that, when a marking of the inner driver shaft 300 is visible through that opening, the instrument 200 is configured for driving a unitary fastener. As another example, a "ROD" label adjacent to the middle opening 452 can indicate to the user that, when a marking of the inner driver shaft 300 is visible through that opening, the instrument 200 is configured for independently driving the rod-locking component of a multi-component fastener. By way of further example, a "POLY" label adjacent to the proximal-most opening 452 can indicate to the user that, when a marking of the inner driver shaft 300 is visible through that opening, the instrument 200 is configured for independently driving the polyaxial-locking component of a multi-component fastener. The markings 454 can be stamped, printed, painted, or otherwise formed on or attached or adhered to an exterior surface of the outer driver shaft 400.

The outer driver shaft 400 can include features to facilitate gripping of the outer driver shaft and application of torque thereto. Such features can allow countertorque to be applied to the outer driver shaft 400 while the inner driver shaft 300 is rotated to tighten or loosen an inner component of a fastener. Exemplary features include textured surfaces, faceted surfaces, knurling, grooved surfaces, etc. As another example, the outer driver shaft 400 can include one or more deployable hinged levers or handles.

Figure 5:
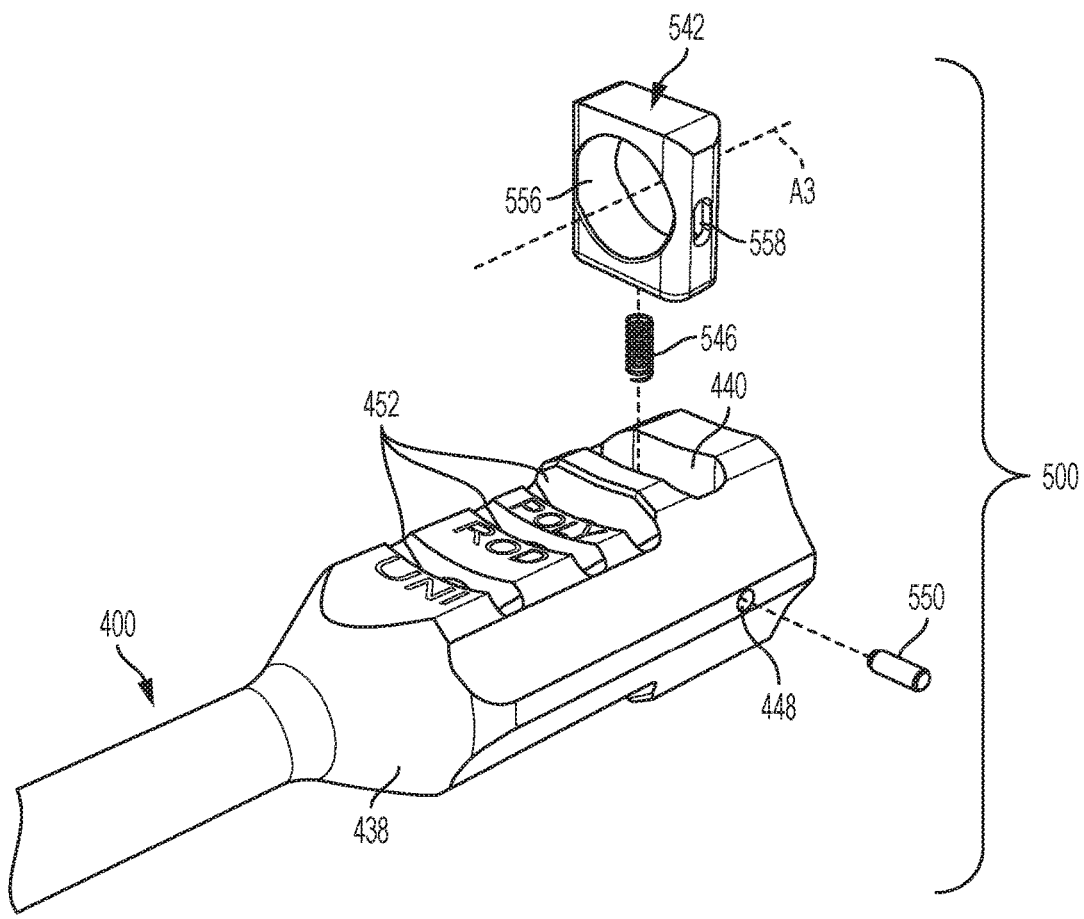
FIG. 5 is an exploded perspective view of a locking mechanism and the outer driver shaft of the instrument of FIG. 2A.

The locking mechanism 500 is shown in greater detail in FIG. 5. As shown, the locking mechanism 500 can include an actuation button 542 with a corresponding button spring 546 and a locking pin 550. The button 542 can include a substantially rectangular-parallelepiped body having proximal and distal abutment surfaces. A cylindrical opening 556 can be formed through the button 542, extending between the proximal and distal surfaces. The opening 556 can include a central longitudinal axis A3. The opening 556 can have a diameter or dimension that is greater than a maximum outer diameter or dimension of the inner driver shaft 300. Accordingly, when the central longitudinal axis A1 of the inner driver shaft 300 is coaxial with the central longitudinal axis A3 of the opening 556, the button 542 does not interfere with longitudinal translation of the inner driver shaft 300 relative to the button. As discussed further below, however, the button 542 can be positioned such that the axis A3 of the opening 556 is offset from the axis A1 of the inner driver shaft 300 and such that the button does interfere with longitudinal translation of the inner driver shaft relative thereto.

The button spring 546 can be partially received within the first bore 444 formed in the bottom of the chamber 440 and partially received within a second bore (not shown) formed in the sidewall of the button 542 that faces the bottom of the chamber. The button spring 546 can thus be effective to bias the button 542 away from the bottom of the chamber 440 such that the button is urged in a direction radially-outward from the housing 438. The locking pin 550 can extend through the opening 448 formed in the sidewall of the housing 438 and into an elongated slot 558 formed in the button 542. The locking pin 550 can thus limit the travel of the button 542 within the chamber 440 to prevent the button from falling out of the housing 438. The locking pin 550 can be welded or otherwise secured to the housing 438 after assembly to prevent inadvertent disassembly.

The button 542 can be slidable within the chamber 440 between at least a first, released position and a second, engaged position. The button 542 can be biased towards the engaged position and can be configured to move from the engaged position to the released position when depressed by a user.

In the released or disengaged position, depression of the button 542 aligns the axis A3 of the button opening 556 with the axis A1 of the inner driver shaft 300 such that longitudinal translation of the inner driver shaft is not limited by the button. Rather, the button 542 is moved out of the path of the projections 312 and the spline 308 formed on the inner driver shaft 300, such that the button does not contact the projections or the spline and such that the button does not restrict longitudinal movement of the inner driver shaft relative to the outer driver shaft 400. In this position, the inner driver shaft 300 is free to translate distally until it contacts the shoulder 436 of the outer driver shaft 400, and is free to translate proximally to be completely removed from the outer driver shaft. Thus, in the disengaged position, the inner driver shaft 300 can be indexed to a desired longitudinal position with respect to the outer driver shaft 400 to set a desired operating mode of the instrument 200.

In the engaged position, the bias of the button spring 546 urges the button 542 upwards such that a portion of the button interferes with at least one of the projections 312 or the spline 308 of the inner driver shaft 300 to prevent certain longitudinal movement of the inner driver shaft relative to the outer driver shaft 400.

Figure 6A:
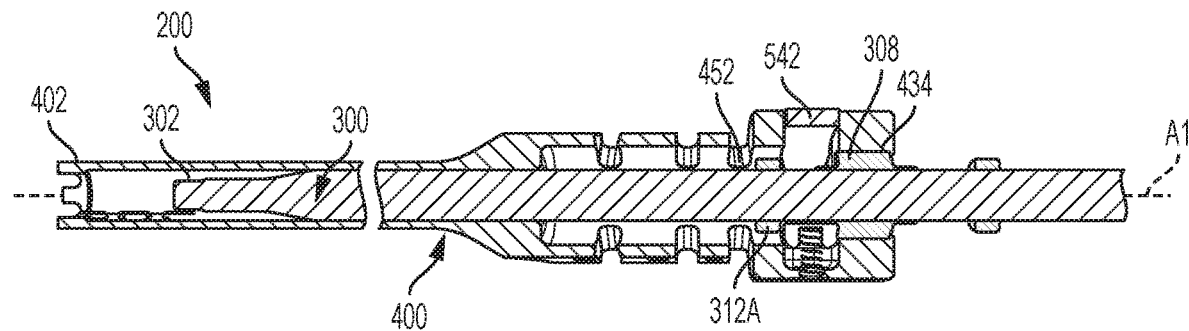
FIG. 6A is a sectional side view of the instrument of FIG. 2A in a first configuration.
Figure 6B:
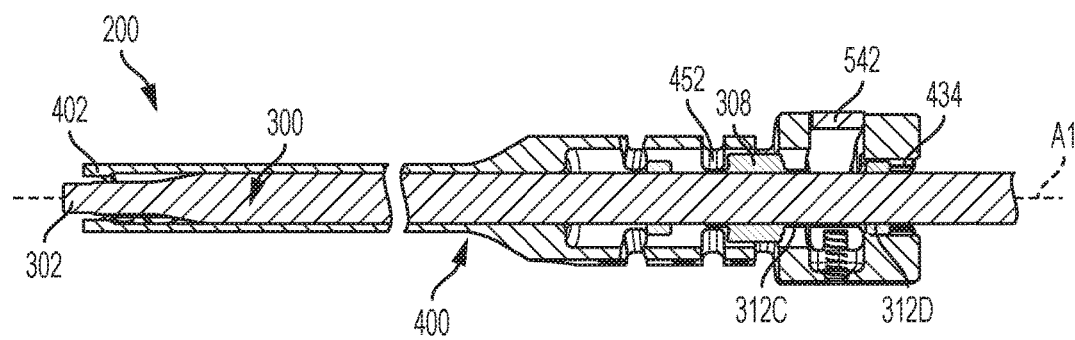
FIG. 6B is a sectional side view of the instrument of FIG. 2A in a second configuration.
Figure 6C:
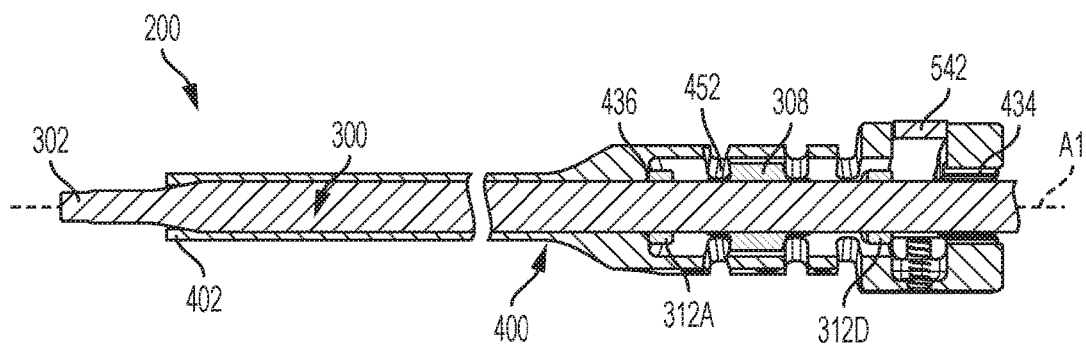
FIG. 6C is a sectional side view of the instrument of FIG. 2A in a third configuration.

FIGS. 6A-6C illustrate three exemplary operating modes of the instrument 200.

In FIG. 6A, the instrument 200 is configured in a first operating mode in which only the outer drive tip 402 is engaged with a fastener. The inner drive tip 302 is retracted proximally from the outer drive tip 402 a sufficient distance to ensure that the inner drive tip does not contact the fastener. In the first operating mode, the spline 308 of the inner driver shaft 300 is inserted into the spline 434 of the outer driver shaft 400. Accordingly, relative rotation between the inner and outer driver shafts 300, 400 about the axis A1 is prevented and torque applied to the inner driver shaft is transferred to the outer driver shaft and, by extension, to a fastener engaged by the outer drive tip 402. The button 542 is disposed in the engaged position, such that the button prevents relative longitudinal movement between the inner and outer driver shafts 300, 400. In particular, the distal abutment surface defined by the teeth 310 of the spline 308 on the inner driver shaft 300 contacts the proximal abutment surface of the button 542 to prevent distal translation of the inner driver shaft relative to the outer driver shaft 400. The proximal abutment surface of the first projection 312A of the inner driver shaft 300 contacts the distal abutment surface of the button 542 to prevent proximal translation of the inner driver shaft 300 relative to the outer driver shaft 400. A marking of the inner driver shaft 300 is longitudinally-aligned with the proximal-most opening 452 of the housing 438, indicating to the user that the instrument 200 is in a "POLY" mode of operation in which application of torque to the instrument is effective to independently tighten or loosen a polyaxial-locking component of a fastener engaged with the instrument.

In FIG. 6B, the instrument 200 is configured in a second operating mode in which both the inner drive tip 302 and the outer drive tip 402 are engaged with a fastener. The inner driver shaft 300 is advanced distally relative to the outer driver shaft 400 as compared to the first operating mode. In the second operating mode, the spline 308 of the inner driver shaft 300 is longitudinally offset from the spline 434 of the outer driver shaft 400. Accordingly, relative rotation between the inner and outer driver shafts 300, 400 about the axis A1 is permitted and torque applied to the inner driver shaft is not transferred to the outer driver shaft. The button 542 is disposed in the engaged position, such that the button prevents relative longitudinal movement between the inner and outer driver shafts 300, 400. In particular, the distal abutment surface of the fourth projection 312D of the inner driver shaft 300 contacts the proximal abutment surface of the button 542 to prevent distal translation of the inner driver shaft 300 relative to the outer driver shaft 400. The proximal abutment surface of the third projection 312C of the inner driver shaft 300 contacts the distal abutment surface of the button 542 to prevent proximal translation of the inner driver shaft 300 relative to the outer driver shaft 400. A marking of the inner driver shaft 300 is longitudinally-aligned with the middle opening 452 of the housing 438, indicating to the user that the instrument 200 is in a "ROD" mode of operation in which application of torque to the instrument is effective to independently tighten or loosen a rod-locking component of a fastener engaged with the instrument.

In FIG. 6C, the instrument 200 is configured in a third operating mode in which only the inner drive tip 302 is engaged with a fastener. The outer drive tip 402 is retracted proximally from the inner drive tip 302 a sufficient distance to ensure that the outer drive tip does not contact the fastener. The inner driver shaft 300 is advanced distally relative to the outer driver shaft 400 as compared to the first operating mode and as compared to the second operating mode. In the third operating mode, the spline 308 of the inner driver shaft 300 is longitudinally offset from the spline 434 of the outer driver shaft 400. Accordingly, relative rotation between the inner and outer driver shafts 300, 400 about the axis A1 is permitted and torque applied to the inner driver shaft is not transferred to the outer driver shaft. The button 542 is disposed in the engaged position, such that the button and the shoulder 436 cooperate to prevent relative longitudinal movement between the inner and outer driver shafts 300, 400. In particular, the distal abutment surface of the first projection 312A of the inner driver shaft 300 contacts the proximal abutment surface of the shoulder 436 to prevent distal translation of the inner driver shaft 300 relative to the outer driver shaft 400. The proximal abutment surface of the fourth projection 312D of the inner driver shaft 300 contacts the distal abutment surface of the button 542 to prevent proximal translation of the inner driver shaft 300 relative to the outer driver shaft 400. A marking of the inner driver shaft 300 is longitudinally-aligned with the distal-most opening 452 of the housing 438, indicating to the user that the instrument 200 is in a "UNI" mode of operation in which application of torque to the instrument is effective to tighten a unitary fastener engaged with the instrument.

The operating mode in which the instrument 200 is configured can be changed by depressing the button 542 to the disengaged position to allow free translational movement of the inner driver shaft 300 and sliding the inner driver shaft relative to the outer driver shaft 400 into the desired operating mode. A user can observe the markings described above to determine when the desired operating mode is selected and then release the button 542 to the engaged position to lock the instrument in said operating mode.

In use, the instrument 200 can be provided initially in a completely assembled state, or can be at least partially assembled by the end user. Assembly of the instrument 200 can be completed by inserting the distal end of the inner driver shaft 300 into the proximal end of the outer driver shaft 400. The inner driver shaft 300 can be slid distally within the outer driver shaft 400 while the button 542 is pressed. The button 542 can be released when the inner driver shaft 300 is in the desired position to retain the inner driver shaft within the instrument 200.

The instrument 200 can be used to apply a fastener to a bone anchor, such as a pedicle or lateral mass screw implanted in a spine of a patient.

Figure 7A:
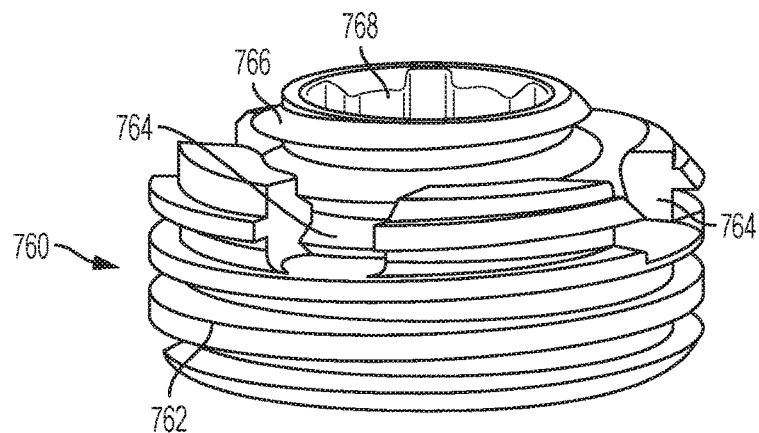
FIG. 7A is a perspective view of a multi-component fastener.
Figure 7B:
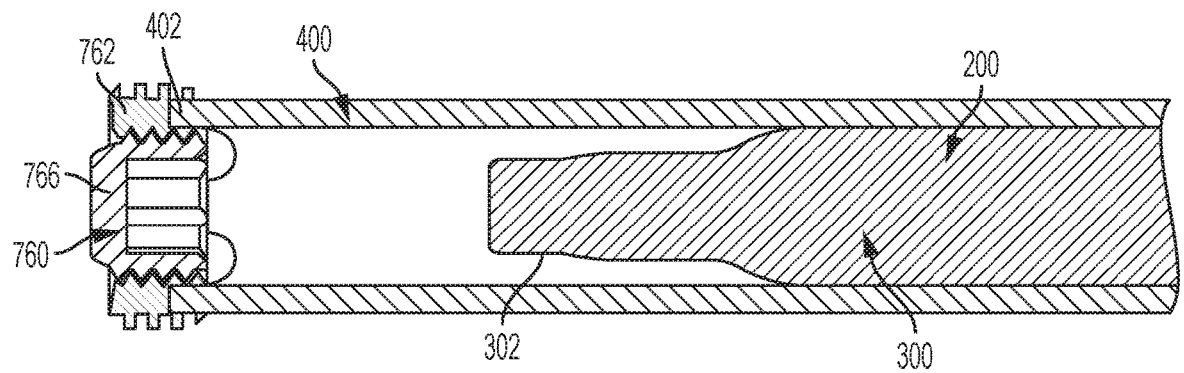
FIG. 7B is a sectional side view of the instrument of FIG. 2A engaged with an outer set screw of the fastener of FIG. 7A.
Figure 7C:
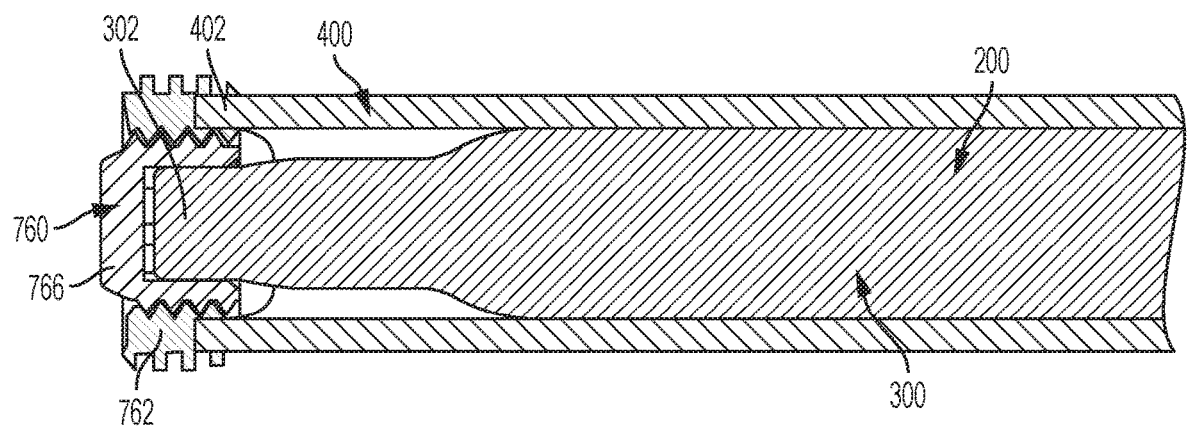
FIG. 7C is a sectional side view of the instrument of FIG. 2A engaged with inner and outer set screws of the fastener of FIG. 7A.

Use of the instrument 200 with an exemplary multi-component fastener 760 is shown in FIGS. 7A-7C. As shown in FIG. 7A, the fastener 760 is a dual set screw that includes an outer set screw 762 with a castle drive feature 764 and an inner set screw 766 with a hexalobe drive recess 768. The fastener 760 can be used with a bone anchor 100 of the type described above, such that tightening the outer set screw 762 locks at least one degree of freedom of the bone anchor (e.g., a polyaxial, uniplanar, or favored-angle degree of freedom) and tightening the inner set screw 766 locks a rod or other fixation element to the bone anchor.

The fastener 760 can be loaded onto and retained to the instrument 200. For example, the inner set screw 766 can be initially positioned such that it protrudes proximally from the outer set screw 762. The instrument 200 can be positioned in the first configuration shown in FIG. 6A and the inner set screw 766 can be inserted into the aperture 424 defined by the distal fingers 422 of the outer driver shaft 400, as shown in FIG. 7B. Insertion of the inner set screw 766 into the aperture 424 can cause the fingers 422 to splay outward and then spring back inward to retain the fastener 760 to the instrument 200, as described in detail above with respect to FIGS. 4E-4G.

With the fastener 760 retained to the instrument 200, the fastener can be positioned in proximity to a bone anchor to which the fastener is to be coupled. For example, the instrument 200 can be used to guide the fastener 760 through a skin incision or a minimally-invasive percutaneous access device towards a bone anchor implanted in a patient's spine. Retention of the fastener 760 to the instrument 200 can advantageously reduce the risk of dropping the fastener down into the incision or access device. While it may be more convenient to use the instrument 200 for both fastener insertion and fastener tightening, it will be appreciated that in some embodiments a separate instrument can be used for fastener insertion and the instrument 200 can be used only for tightening, in which case the retention features of the instrument 200 can be omitted.

With the instrument 200 still positioned in the first configuration of FIG. 6A, torque can be applied to the inner driver shaft 300 to transfer the torque to the outer driver shaft 400 and to rotate the outer set screw 762 relative to the bone anchor. Such rotation can be effective to tighten the outer set screw 762 to the bone anchor to lock a degree of freedom of the bone anchor, or to loosen the outer set screw from the bone anchor to mobilize a previously locked degree of freedom of the bone anchor. Since the inner driver shaft 300 is retracted proximally and disengaged from the fastener 760, rotation of the instrument 200 only tightens the outer set screw 762 and does not produce any relative rotation between the inner and outer set screws 766, 762.

When desired by the user, the instrument 200 can be moved to the second position shown in FIG. 6B to advance the inner driver shaft 300 distally into engagement with the drive recess 768 of the inner set screw 766, as shown in FIG. 7C. Torque can be applied to the inner driver shaft 300 to rotate the inner set screw 766 relative to the outer set screw 762 and relative to the bone anchor. Such rotation can be effective to tighten the inner set screw 766 to the bone anchor to lock a rod to the bone anchor, or to loosen the inner set screw from the bone anchor to mobilize a previously locked rod. Since the outer driver shaft 400 does not rotate with the inner driver shaft 300 and remains engaged with the outer set screw 762, the outer driver shaft can be used to apply countertorque when tightening or loosening the inner set screw 766. For example, a user can grasp the outer driver shaft 400 manually or with a wrench or other tool while the inner driver shaft 300 is rotated.

When the fastener 760 is finally-tightened to the bone anchor, or at any other time desired by the user, the fastener can be released from the instrument 200 and the instrument can be removed from the surgical site. Release of the fastener 760 can be achieved, for example, by applying a proximally-directed axial force to the instrument 200 while the fastener is coupled to the implanted bone anchor, thereby deflecting the fingers 422 outward to release the fastener. The instrument 200 can be used with compression or distraction instruments before or during final tightening to achieve a desired correction or relative vertebral position.

Figure 8A:
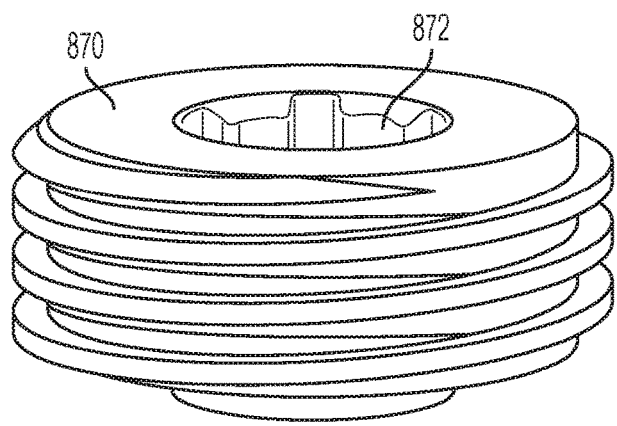
FIG. 8A is a perspective view of a unitary fastener.
Figure 8B:
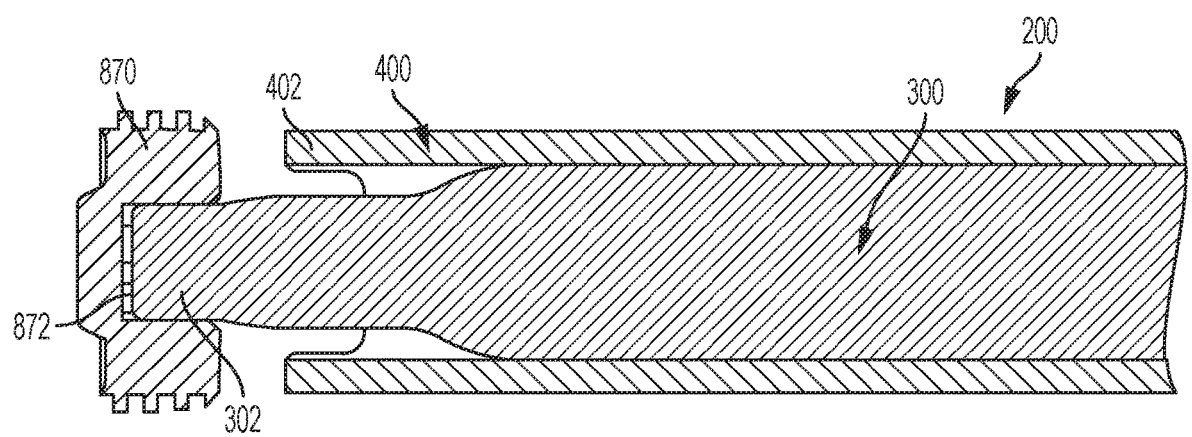
FIG. 8B is a sectional side view of the instrument of FIG. 2A engaged with the fastener of FIG. 8A.

Use of the instrument 200 with an exemplary unitary fastener 870 is shown in FIGS. 8A-8B. As shown in FIG. 8A, the fastener 870 is a unitary set screw that includes an external thread and a hexalobe drive recess 872. The fastener 870 can be used with a bone anchor 100 of the type described above, such that tightening the set screw locks at least one degree of freedom of the bone anchor (e.g., a polyaxial, uniplanar, or favored-angle degree of freedom) and locks a rod to the bone anchor.

The fastener 870 can be loaded onto and retained to the instrument 200. For example, the instrument 200 can be positioned in the third configuration shown in FIG. 6C and the drive tip 302 of the inner driver shaft 300 can be inserted into the drive recess 872 of the fastener 870, as shown in FIG. 8B. The drive tip 302 can be configured to retain the fastener 870 to the instrument 200. For example, the drive tip 302 can be magnetic or can include a tapered portion, spring fingers, or other retention features.

With the fastener 870 retained to the instrument 200, the fastener can be positioned in proximity to a bone anchor to which the fastener is to be coupled. For example, the instrument 200 can be used to guide the fastener 870 through a skin incision or a minimally-invasive percutaneous access device towards a bone anchor implanted in a patient's spine. Retention of the fastener 870 to the instrument 200 can advantageously reduce the risk of dropping the fastener down into the incision or access device. While it may be more convenient to use the instrument 200 for both fastener insertion and fastener tightening, it will be appreciated that in some embodiments a separate instrument can be used for fastener insertion and the instrument 200 can be used only for tightening, in which case the retention features of the instrument 200 can be omitted.

With the instrument 200 still positioned in the third configuration of FIG. 6C, torque can be applied to the inner driver shaft 300 to rotate the set screw 870 relative to the bone anchor. Such rotation can be effective to tighten the set screw 870 to the bone anchor to lock a degree of freedom of the bone anchor and lock a rod to the bone anchor, or to loosen the set screw from the bone anchor to mobilize the rod and a previously locked degree of freedom of the bone anchor. Since the outer driver shaft 400 is retracted proximally and disengaged from the fastener 870, it does not interfere with tightening or loosening of the fastener.

When the fastener 870 is finally-tightened to the bone anchor, or at any other time desired by the user, the fastener can be released from the instrument 200 and the instrument can be removed from the surgical site. Release of the fastener 870 can be achieved, for example, by applying a proximally-directed axial force to the instrument 200 while the fastener is coupled to the implanted bone anchor. The instrument 200 can be used with compression or distraction instruments before or during final tightening to achieve a desired correction or relative vertebral position.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

It will be appreciated from the foregoing that the instrument 200 can allow fastener loading, fastener tightening, fastener loosening, and/or fastener countertorque to be performed with multiple different types of fasteners or independently for multiple different components of a fastener using a single instrument. In some embodiments, the above functions can be performed without ever having to release the fastener from the instrument 200. It will further be appreciated that the instrument 200 can provide a simple and reliable way of loading the fastener and retaining the fastener to prevent dropping while at the same time being strong enough to apply the high levels of torque typically required for final tightening a spinal fixation construct, e.g., at least about 80 inch pounds. The instrument 200 can advantageously reduce the number of instruments required for a particular procedure, and make the procedure less cumbersome and time-consuming by reducing or eliminating the need to switch between multiple instruments.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of advancing a fastener into a bone anchor implanted in a bone such as the pedicle or lateral mass of a human spine, it will be appreciated that the methods and devices disclosed herein can be used with any human or animal bone, implant, non-living object, and so forth.

Although specific embodiments are described above, it should be understood that numerous changes may be made within the spirit and scope of the concepts described. For example, in some embodiments, the "UNI" configuration shown in FIG. 6C can be omitted and the instrument 200 can include only the "POLY" and "ROD" configurations of FIGS. 6A-6B. As another example, the instrument 200 can include a bias spring or other element configured to bias the inner driver shaft 300 relative to the outer driver shaft 400, e.g., towards the configuration of FIG. 6A or towards the configuration of FIG. 6B.

The invention claimed is:

1. A driver instrument, comprising:
an inner driver shaft having an inner drive tip; and
an outer driver shaft in which the inner driver shaft is at least partially disposed, the outer driver shaft having an outer drive tip, the outer drive tip comprising a plurality of distally extending teeth;
wherein the instrument has:
a first configuration in which the inner drive tip is retracted proximally from the outer drive tip and an input torque applied to the inner driver shaft is transferred to the outer driver shaft and the outer drive tip; and
a second configuration in which the inner drive tip is advanced distally from the outer drive tip and an input torque applied to the inner driver shaft is not transferred to the outer driver shaft or the outer drive tip,
wherein, in the first configuration, the plurality of distally extending teeth of the outer drive trip are configured to extend into an outer set screw of a fastener and apply torque to the outer set screw independently from an inner set screw of the fastener, and
wherein, in the second configuration, the inner drive tip is configured to apply torque to the inner set screw of the fastener independently from the outer set screw.

2. The instrument of claim 1, wherein one or more of the plurality of distally extending teeth of the outer drive trip comprise a projection extending radially inward and configured to positively interlock with the fastener.

3. The instrument of claim 1, wherein the instrument is movable between the first and second configurations by translating the inner driver shaft longitudinally relative to the outer driver shaft.

4. The instrument of claim 1, wherein the inner driver shaft includes an anti-rotation feature configured to selectively engage a corresponding anti-rotation feature of the outer driver shaft to lock relative rotation between the inner and outer driver shafts and transfer torque between the inner and outer driver shafts.

5. The instrument of claim 4, wherein the anti-rotation feature of the inner driver shaft comprises an external spline and the anti-rotation feature of the outer driver shaft comprises an internal spline.

6. The instrument of claim 1, wherein the outer driver shaft is configured to retain a fastener to the instrument.

7. The instrument of claim 6, wherein the outer driver shaft includes a plurality of resilient fingers extending distally therefrom, at least one of the fingers being configured to clamp onto a fastener received within a distal aperture of the outer driver shaft.

8. The instrument of claim 7, wherein at least one of the fingers includes a projection extending radially-inward therefrom and configured to be received within a corresponding recess of a fastener.

9. The instrument of claim 7, wherein each finger interlocks with an adjacent finger at multiple points along its length.

10. The instrument of claim 6, wherein the outer drive shaft has a cut-out formed therein, the cut-out being shaped such that a first finger on one side of the cut-out has an edge that defines one or more recesses, and a second finger on the opposite side of the cut-out has an edge that defines one or more projections, each of the projections being disposed within a corresponding one of the recesses, the edges being defined by the same cut-out.

11. The instrument of claim 10, wherein each projection includes a head portion that is enlarged as compared to a neck portion of the recess in which the projection is disposed, such that the head portion cannot pass through the neck portion.

12. A driver instrument, comprising:
an inner driver shaft having an inner drive tip; and
an outer driver shaft in which the inner driver shaft is at least partially disposed, the outer driver shaft having an outer drive tip;
wherein the instrument has:
a first configuration in which the inner drive tip is retracted proximally from the outer drive tip and an input torque applied to the inner driver shaft is transferred to the outer driver shaft and the outer drive tip;
a second configuration in which the inner drive tip is advanced distally from the outer drive tip and an input torque applied to the inner driver shaft is not transferred to the outer driver shaft or the outer drive tip; and
a locking mechanism configured to selectively lock the instrument in the first configuration or the second configuration.

13. The instrument of claim 12, wherein the locking mechanism comprises a button movably coupled to the outer driver shaft, the button having an engaged position in which the button interferes with relative longitudinal translation between the inner and outer driver shafts and a disengaged position in which the button does not interfere with relative longitudinal translation between the inner and outer driver shafts.

14. The instrument of claim 13, wherein the button defines an opening through which the inner driver shaft extends.

15. The instrument of claim 14, wherein a central longitudinal axis of the opening is collinear with a central longitudinal axis of the inner driver shaft when the button is in the disengaged position and wherein the central longitudinal axis of the opening is offset from the central longitudinal axis of the inner driver shaft when the button is in the engaged position.

16. A system, comprising:
a driver instrument, comprising:
an inner driver shaft having an inner drive tip; and
an outer driver shaft in which the inner driver shaft is at least partially disposed, the outer driver shaft having an outer drive tip;
wherein the instrument has:
a first configuration in which the inner drive tip is retracted proximally from the outer drive tip and an input torque applied to the inner driver shaft is transferred to the outer driver shaft and the outer drive tip; and
a second configuration in which the inner drive tip is advanced distally from the outer drive tip and an input torque applied to the inner driver shaft is not transferred to the outer driver shaft or the outer drive tip; and
a fastener having an outer set screw with a first drive feature and an inner set screw threadably mounted in the outer set screw and having a second drive feature;
wherein the outer drive tip of the instrument is configured to apply torque to the outer set screw via the first drive feature and the inner drive tip of the instrument is configured to apply torque to the inner set screw via the second drive feature.

17. A driver instrument, comprising:
an inner driver shaft having an inner drive tip; and
an outer driver shaft in which the inner driver shaft is at least partially disposed, the outer driver shaft having an outer drive tip;
wherein the instrument has:
a first configuration in which the inner drive tip is retracted proximally from the outer drive tip and an input torque applied to the inner driver shaft is transferred to the outer driver shaft and the outer drive tip; and
a second configuration in which the inner drive tip is advanced distally from the outer drive tip and an input torque applied to the inner driver shaft is not transferred to the outer driver shaft or the outer drive tip,
wherein the outer driver shaft is configured to retain a fastener to the instrument,
wherein the outer driver shaft includes a plurality of resilient fingers extending distally therefrom, at least one of the fingers being configured to clamp onto a fastener received within a distal aperture of the outer driver shaft, and each finger interlocks with an adjacent finger at multiple points along its length.

* * * * *